United States Patent [19]

Sindrey

[11] Patent Number: 5,208,041

[45] Date of Patent: May 4, 1993

[54] ESSENTIALLY PURE HUMAN PARATHYROID HORMONE

[75] Inventor: Dennis R. Sindrey, Etobicoke, Canada

[73] Assignees: Allelix Biopharmaceuticals Inc.; Glaxo Canada Inc., both of Mississauga, Canada

[21] Appl. No.: 707,114

[22] Filed: May 23, 1991

[51] Int. Cl.$^5$ ............................................. A61K 37/24
[52] U.S. Cl. ...................................... 424/562; 514/2; 514/21; 530/324; 435/71.2
[58] Field of Search ...................... 424/562; 514/2, 21; 530/324; 435/71.2

[56] References Cited

U.S. PATENT DOCUMENTS 3,886,132  5/1975  Brewer et al. ...................... 530/399

FOREIGN PATENT DOCUMENTS 0357391  8/1989  European Pat. Off. .

OTHER PUBLICATIONS

Rabbani et al. CA 109:5186 (1988).
Fairwell et al. CA 98: 198739 (1983).
Sung, et al, "Specific Degenerate Codons Enhanced Selective Expression Of Human Parathyroid Hormone in *Escherichia Coli*", *The Journal of Biological Chemistry*, vol. 266, pp. 2831-2835, (1991).

Rabbani, et al, "Recombinant Human Parathyroid Hormone Synthesized in *Escherichia Coli*", *The Journal Of Biological Chemistry*, vol. 263, pp. 1307-1313, (1988).

Hogset, et al, "Expression and Characterization Of A Recombinant Human Parathyroid Hormone Secreted By *Escherichia Coli* Employing the Staphylococcal Protein A Promoter And Signal Sequence", *The Journal Of Biological Chemistry*.

Kimura, et al, "Solution Synthesis Of [ASN$^{76}$]-Human Parathyroid Hormone (1-84)", *Biochemical And Biophysical Research Communications*, vol. 114, pp. 493-499, (1983).

Primary Examiner—Douglas W. Robinson
Assistant Examiner—Jean C. Witz
Attorney, Agent, or Firm—Foley & Lardner

[57] ABSTRACT

Human parathyroid hormone is provided in an ultrapure form characterized by the absence of protein contaminants detectable by capillary electrophoresis analysis. A method for obtaining such ultrapure human parathyroid hormone is also described.

21 Claims, 3 Drawing Sheets

FIG. IA
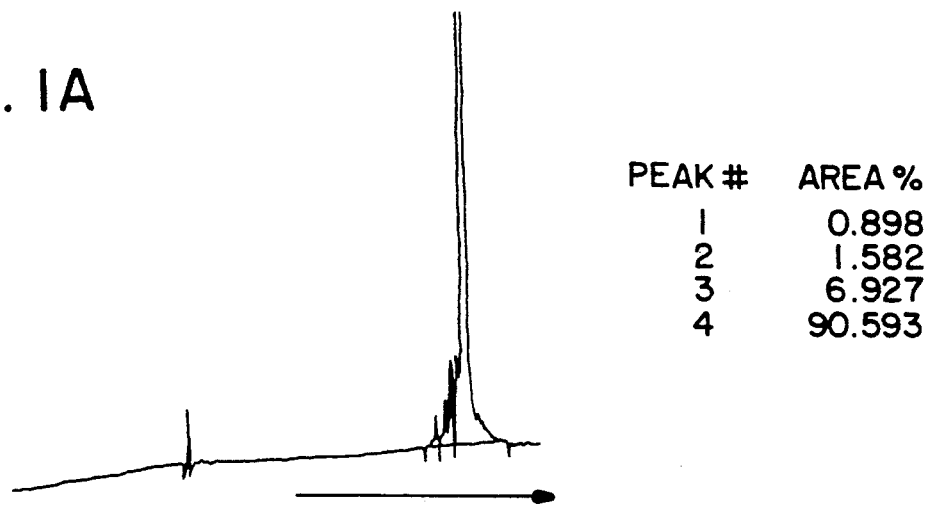
| PEAK # | AREA % |
|---|---|
| 1 | 0.898 |
| 2 | 1.582 |
| 3 | 6.927 |
| 4 | 90.593 |
FIG. IB
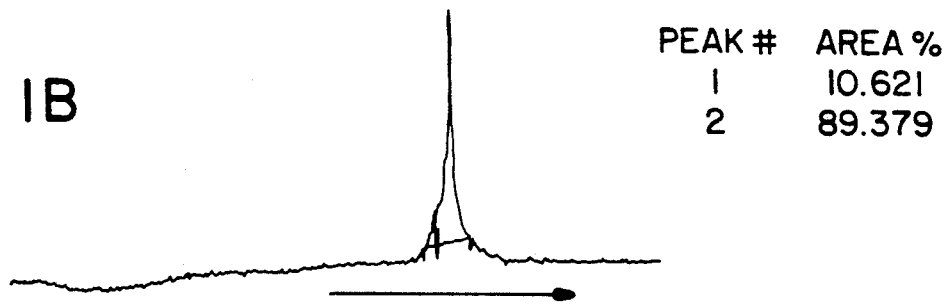
| PEAK # | AREA % |
|---|---|
| 1 | 10.621 |
| 2 | 89.379 |
FIG. IC
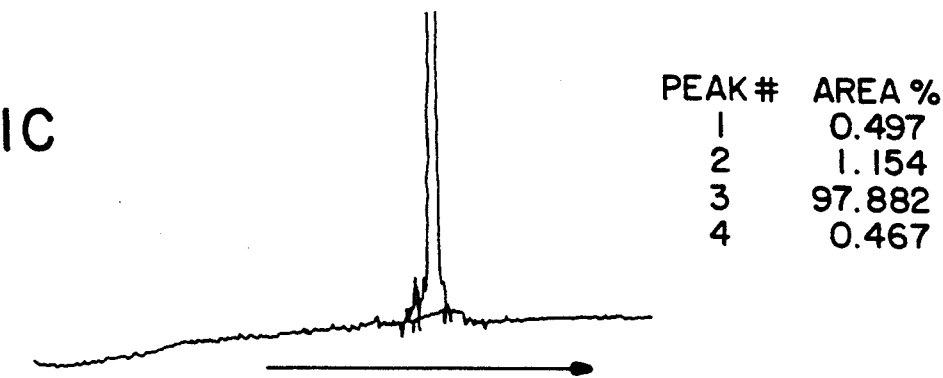
| PEAK # | AREA % |
|---|---|
| 1 | 0.497 |
| 2 | 1.154 |
| 3 | 97.882 |
| 4 | 0.467 |

| PEAK # | AREA % |
|---|---|
| 1 | 0.898 |
| 2 | 1.582 |
| 3 | 6.927 |
| 4 | 90.593 |

| PEAK # | AREA % |
|---|---|
| 1 | 100. |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: homo sapiens ( v i i ) IMMEDIATE SOURCE:
        ( B ) CLONE: hPTH ( x i ) SEQUENCE DESCRIPTION: SEQ ID NO:1:

```
Ser  Val  Ser  Glu  Ile  Gln  Leu  Met  His  Asn  Leu  Gly  Lys  His  Leu  Asn
 1              5                        10                         15

Ser  Met  Glu  Arg  Val  Glu  Trp  Leu  Arg  Lys  Lys  Leu  Gln  Asp  Val  His
                20                        25                    30

Asn  Phe  Val  Ala  Leu  Gly  Ala  Pro  Leu  Ala  Pro  Arg  Asp  Ala  Gly  Ser
           35                    40                        45

Gln  Arg  Pro  Arg  Lys  Lys  Glu  Asp  Asn  Val  Leu  Val  Glu  Ser  His  Glu
      50                    55                        60

Lys  Ser  Leu  Gly  Glu  Ala  Asp  Lys  Ala  Asn  Val  Asp  Val  Leu  Thr  Lys
```

|     65     |     70     |     75     |     80     |
|---|---|---|---|
|            | Ala Lys Ser Gln |        |            |

ESSENTIALLY PURE HUMAN PARATHYROID HORMONE

BACKGROUND TO THE INVENTION

Human parathyroid hormone, or hPTH, is a protein product of the parathyroid glands that exerts various physiological effects. Of particular clinical significance is its anabolic effect on bone tissue, and the possibility that PTH therapy can slow or reverse the progression of osteoporosis, and be of benefit in the treatment of related bone disorders.

As a prelude to using hPTH as a pharmaceutical product, it is necessary for many reasons to provide the protein in essentially pure form. For instance, the use in clinical trials of PTH that is essentially pure will permit observed effects to be attributed solely to PTH and not to some structurally related contaminant. Also, obtaining hPTH in essentially pure form will provide for greater specific activity i.e. highest potency per unit amount of hPTH, and permit administration of the smallest possible dosage size to treat a given indication. Furthermore, removal of contaminants will effectively reduce the possibility of side effects, which is especially important when PTH is used to treat chronic ailments such as osteoporosis.

One method currently used to purify proteins, and to analyze protein purity, is reversed phase high performance liquid chromatography (RP-HPLC). Like other HPLC techniques, the reversed phase approach exploits variability in the rates at which specific proteins migrate through a bed of silica microspheres. In the reversed phase HPLC technique, however, alkylated silica microspheres are used, and migrating proteins are subjected to a two phase solvent system which exploits protein charge and accents separation. Most typically, the solvent system consists of a water phase and an organic phase typically containing acetonitrile and an ion-pairing agent (also known as a charge modifier) such as trifluoroacetic acid (TFA), the relative proportions of which are altered gradiently by automated blending as the protein sample migrates through the column. When analyzed by this technique, a protein preparation which elicits but a single detectable protein species (measured by UV absorbance either at 214 nm or at 280 nm) is deemed to consist of one protein species, and is thus characterized as an essentially pure protein. Proteins exhibiting this degree of purity are sometimes characterized as being of "HPLC-grade".

REFERENCE TO THE PRIOR ART

The reversed phase HPLC technique has been used to purify and to assess the purity of human PTH obtained from various sources. By applying the technique of peptide synthesis, synthetic human PTH has been produced by Kimura et al as reported in Biochem. Biophys. Res. Commun., 1983, 114(2):493, and is also available commercially from Bachem Inc. (1987–1988 catalogue #PCAL175). According to this supplier, the human PTH product is greater than 99% pure when analyzed by reversed phase HPLC using an acetonitrile and water in the presence of TFA as the ion-pairing agent.

More recently, HPLC-grade human PTH has been recovered from genetically engineered bacterial hosts. For example, Hogset et al (J. Biol. Chem., 1990, 265(13):7338) describe secretion of human PTH from an E. coli transformant. The human PTH so produced is recovered in culture broth filtrate which is subjected to ion exchange chromatography and then fractionated by reversed phase HPLC, using the conventional water-/acetonitrile solvent system supplemented with TFA as ion-pairing agent. E. coli-produced human PTH has also been generated as an intracellular product, as described by Rabbani et al in J. Biol. Chem., 1988, 263(3):1307. Acid-extracted PTH was subjected to RP-HPLC using the conventional acetonitrile/TFA solvent system, and main peaks were then gel filtered and subjected individually again to reversed phase HPLC using a water/acetonitrile solvent system supplemented with heptaflurorbutyric acid (HFBA) as ion-pairing agent. Like trifluroacetic acid, HFBA is another member of the class of anionic ion pairing agents. The material so fractionated was then subjected again to the TFA-based RP-HPLC fractionation and then ultimately collected following passage through a gel filtration column, to obtain HPLC-grade PTH. Sung et al have also reported E. coli-based production of human PTH (see J. Biol. Chem., 1991, 266(5):2831). These authors purified the human PTH product by RP-HPLC using the conventional acetonitrile/water solvent system supplemented with TFA.

It has now been determined, however, that PTH compositions exhibiting HPLC-grade purity in fact contain protein impurities detectable by the more sensitive analytical technique of capillary electrophoresis (CE). It is accordingly an object of the present invention to provide human PTH in a form that is essentially free from protein contaminants detectable by capillary electrophoresis. It is another object of the present invention to provide a method for obtaining human PTH in essentially pure form. It is a further object of the present invention to provide a pharmaceutical composition which contains essentially pure human PTH.

SUMMARY OF THE INVENTION

The present invention provides human PTH in essentially pure form, i.e., in a form that is essentially free from protein contaminants, as determined by capillary electrophoresis analysis. The capillary electrophoresis technique offers a more sensitive measure of PTH purity, as demonstrated herein by its ability to detect impurities in human PTH preparations determined to be pure by conventionally applied HPLC analysis.

In one aspect of the present invention, there is provided a composition which consists of pure human PTH and is essentially free from protein contaminants detectable by capillary electrophoresis. In one specific embodiment of this aspect of the present invention, the essentially pure human PTH is provided in lyophilized form.

According to another aspect of the present invention, there is provided a process for preparing a pharmaceutical composition, which comprises the step of combining the pure human PTH with a pharmaceutically acceptable carrier. In a related aspect of the present invention, there is provided a pharmaceutical composition comprising the pure human PTH and a pharmaceutically acceptable carrier. According to one specific embodiment of this aspect of the present invention, the pharmaceutical composition further comprises a reducing agent in an amount useful to enhance oxidative stability of the PTH contained therein. The composition may also comprise a second therapeutic agent, if desired.

In a further aspect of the present invention, there is provided a method for purifying human PTH, which comprises the step of fractionating a partially purified human PTH preparation by reversed phase HPLC in the presence of a cationic ion-pairing agent, to separate human PTH from protein contaminants resident in the preparation, and then collecting essentially pure human PTH.

These and other aspects of the present invention are now described in greater detail, with reference to the accompanying drawings, in which:

BRIEF REFERENCE TO THE DRAWINGS

FIG. 1 provides CE profiles of HPLC-grade PTH samples obtained from the following sources; excreted bacterial PTH (1A), commercially available, synthetic PTH (1B), and intracellular bacterial PTH (1C);

FIG. 2 provides HPLC profiles of a PTH sample run in the presence of HFBA (2A), and in the presence of TEAP (2B, 2C); and FIG. 3 provides CE profiles of a PTH sample fractionated by reversed phase HPLC in HFBA (3A) and in TEAP (3B).

DETAILED DESCRIPTION OF THE INVENTION AND ITS PREFERRED EMBODIMENTS

Figure 2A:
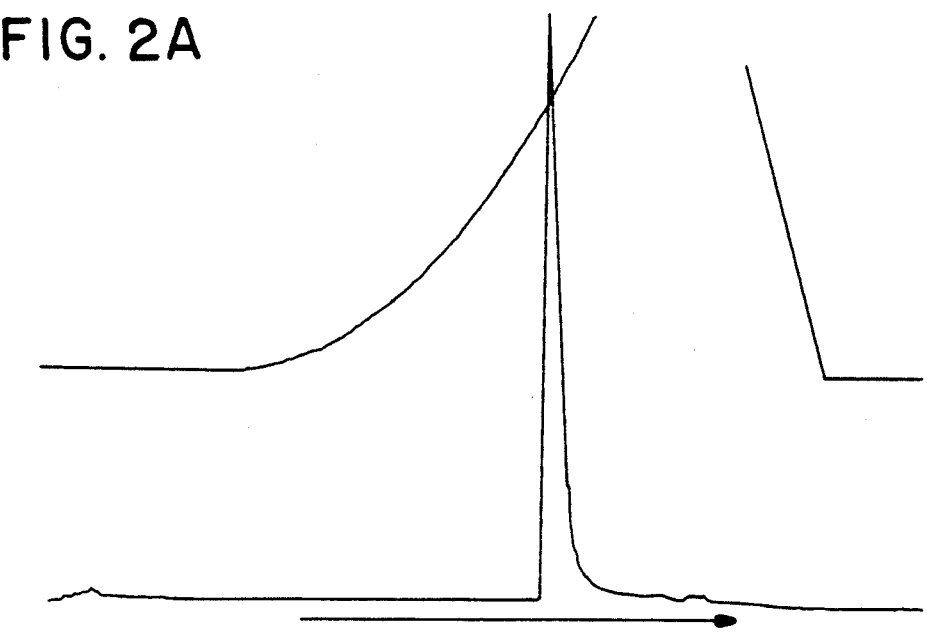

The invention relates to human PTH in a form that is essentially free from protein contaminants detectable by capillary electrophoresis (CE). For brevity, PTH exhibiting this purity is sometimes herein referred to as "CE-grade" human PTH, or as "essentially pure" human PTH.

For the purposes of the present specification, the terms "hPTH", "human PTH" and "human parathyroid hormone"are used interchangably with reference to a non-glycosylated protein consisting essentially of 84 alpha-amino acid residues arranged by amide linkage in the sequence (SEQ ID NO:1) identified below:

H—Ser—Val—Ser—Glu—Ile—Gln—Leu—Met—His—Asn—Leu—Gly—

Lys—His—Leu—Asn—Ser—Met—Glu—Arg—Val—Glu—Trp—Leu—

Arg—Lys—Lys—Leu—Gln—Asp—Val—His—Asn—Phe—Val—Ala—

Leu—Gly—Ala—Pro—Leu—Ala—Pro—Arg—Asp—Ala—Gly—Ser—

Gln—Arg—Pro—Arg—Lys—Lys—Glu—Asp—Asn—Val—Leu—Val—

Glu—Ser—His—Glu—Lys—Ser—Leu—Gly—Glu—Ala—Asp—Lys—

Ala—Asp—Val—Asn—Val—Leu—Thr—Lys—Ala—Lys—Ser—Gln—OH.

Those skilled in the art of protein chemistry will appreciate that slight variations in structure may occur, depending to a great extent on the nature of the PTH source. Celluarly-derived human PTH, i.e. hPTH derived either from parathyroid tissue or from microbial sources, may possess a small proportion of C-terminally amidated protein or C-terminally truncated protein, for example. On the other hand, synthetically-derived human PTH may contain a small proportion of PTH molecules that incorporate amino acids bearing modified alpha carbon side chains. CE-grade human PTH may contain PTH molecules having such modifications, provided of course that they are present in amounts small enough as to be undetectable by capillary electrophoresis analysis.

The CE-grade human PTH of the present invention can be characterized, more particularly, by migration as a single absorbance peak at 214 nm when subjected to capillary electrophoresis analysis. The capillary electrophoresis technique separates proteins on the basis of mass/charge ratio within a capillary having a bore of miniscule diameter, as reviewed generally by Gordon et al in Science, 1988, 242:224. Briefly, aqueous samples of the protein preparation to be analyzed are drawn by vacuum into the capillary and subjected to an electric field, with subsequent migration of protein species through the capillary being monitored by detecting absorbance desirably at 214 nm. In the specific case of human PTH, resolution of protein species is suitably achieved using preparations containing from about 0.2 mg/ml to about 1.0 mg/ml in an aqueous vehicle buffered by phosphate to about pH2. The rate at which sample is drawn is uniform, though it is desirable to maintain sample draw for from 2 to 10 seconds depending on initial purity of the sample, so that contaminants, if present, are loaded in detectable amounts.

In addition to exhibiting CE-grade purity, the essentially pure human PTH of the present invention is characterized by a remarkably low EC50 of not greater than two nanomolar i.e., an EC50 of about $1.0\pm0.2$ nM, as determined in the UMR 106-based adenylate cyclase assay, described for example by Rabbani et al in Endocrinology, 1988, 123:2709. For comparison, HPLC-grade PTH obtained as described by Rabbani et al, supra, is said to possess an EC50 in this assay of not less than 3 nM. This in vitro bioassay measures quantitatively the extent to which a given PTH preparation stimulates adenylate cyclase production within rat osteosarcoma cells of the UMR-106 lineage. As used herein, the term "EC50"refers to the concentration (measured in molarity) of a given hPTH preparation required to elicit a half-maximal response in the UMR-106 based adenylate cyclase assay.

The CE-grade human PTH is also characterized by a molecular weight of about 9,425 daltons as determined by ion spray mass spectrometric analysis, which is virtually equivalent to its theoretical molecular weight of 9424.7.

Human PTH having the characteristics just described can be obtained by subjecting a partially purified human PTH preparation to reversed phase high performance liquid chromatography in the presence of a cationic ion-pairing agent. Those skilled in the art will appreciate that ion-pairing agents employed conventionally to achieve protein separation by RP-HPLC include such anionic modifiers as heptafluorobutyric acid (HFBA) and, more commonly, trifluoroacetic acid (TFA). As is demonstrated herein, however, these ion-pairing agents and especially HFBA do not provide the resolution required to separate human PTH from structurally-related protein contaminants, so that human PTH eluting from the chromatographic column can be collected independently of protein contaminants. It has been found that cationic ion-pairing agents, especially amine-based ion-pairing agents (known as also "charge modifiers") possess the charge characteristics best suited to providing this resolution.

One aspect of the present invention thus resides in a method for obtaining essentially pure human PTH, which comprises the step of subjecting a preparation of partially purified PTH to fractionation by reversed phase high performance liquid chromatography in the presence of a cationic ion-pairing agent. Essentially pure PTH is then recovered by collecting selectively the main protein peak migrating through the column (as determined by absorbance at 280 nm or more preferably at 214 nm), to the exclusion of contaminants represented in the neighbouring smaller protein peaks.

Among the cationic ion-pairing agents that can be used are the amine-based agents including di- and tri-lower alkyl amines such as trimethylamine, triethylamine, tributylamine and dipropylamine. Especially preferred as the ion-pairing agent is triethylamine. The ion-pairing agent may be used in salt form, and triethylamine phosphate, prepared by mixing triethylamine and phosphoric acid, is preferred in this regard. Further, the ion-pairing agent optionally in salt form may be formulated in an alkanol solvent, such as methanol, propanol or isopropanol, if desired, or in organic acid such as formic acid.

When salts of the amine-based ion-pairing agent are used, it is desirable, as a final step in the PTH purification process, to remove the ion-pairing agent by desalting the material collected from the reversed phase HPLC column. Desalting can be performed by subjecting the collected sample to any one of a variety of suitable desalting methods, such as by gel filtration, ultrafiltration, or reversed phase HPLC in which a volatile ion-paring agent is employed, such as the conventional ion-paring agents trifluoroacetic acid (TFA) and heptafluoroacetic acid (HFBA).

The amine-based ion-pairing agent is incorporated, and the RP-HPLC purification process is performed, in the manner conventional when other ion-pairing agents are used. The two solvent solutions to be blended gradiently during the HPLC run are first prepared, to provide a "solvent A" solution containing water and the amine-based ion-pairing agent, and a "solvent B" solution that comprises water, the amine-based ion-pairing agent, and about 80% of an organic component such as acetonitrile, methanol or 1-propanol. Best results are obtained using acetonitrile. Each solvent is prepared by mixing commercially available HPLC-grade reagents and then filtering, for example through a 0.45 micron filter, followed by degassing to remove oxygen, all according to conventional protocols.

When triethylamine phosphate (TEAP) is used as the ion-pairing agent, solvent concentrations of TEAP in the range from 0.05 to 1.0% by volume may be used, with best separations being achieved at around 0.4% TEAP by volume. In a particularly preferred embodiment of the present invention, therefore, PTH purification is achieved by reversed phase HPLC using as solvent solutions a solvent A which consists of 100% water to which has been added 0.4% triethylamine and 0.4% phosphoric acid (85%), and a solvent B which consists of 80% acetonitrile to which has been added 0.4% triethylamine and an amount of phosphoric acid (85%), generally about 0.4%, sufficient to render the pH equivalent to that in solvent A.

Apart from incorporation of the amine-based modifier in the solvents, fractionation of preparations containing substantially pure human PTH can be achieved using HPLC devices that are available commercially, in the manner conventional for reversed phase HPLC techniques (see for example CRC Handbook of HPLC for the Separation of Amino Acids, Peptides and Proteins, Volume 1, 1984, CRC Press Inc.). Columns within which the fractionation occurs may be packed for example with silica beads bearing alkyl groups of a uniform length in the range from C4 to C18, with C18 being preferred for PTH separation. It has been found that columns packed with C-18 beads having a uniform size of about 5 microns and a pore size of about 300 angstroms are well suited for PTH purification. Such columns are available commercially, as cartridges for incorporation into HPLC machines, from Rainin Instrument Co., Inc., Woburn, Mass., and are sold under the trade name "Dynamax".

Fractionation of substantially purified PTH is then achieved by injecting a sample of the preparation into the machine, and then adjusting the relative blend of solvents A and B, as desired. While it is possible to generate a linear gradient from 100% solvent A through to 100% solvent B, a gradient that is more desirable for PTH fractionation has been found consist of a gradient that proceeds from 70% A/30% B through 40%A/60%B and returning to 70%A/30%B. This gradient is ideally established using a flow rate of about 1 ml of solvent per minute of injection. Under these conditions, essentially pure PTH elutes at about 26 minutes, and in about 35% acetontrile.

The advantage of using triethylamine as the ion-pairing agent is evident when, as is conventional, migration of protein through the HPLC column is monitored by absorbance at 214 nm. As is shown in the Figures herein, contaminants in the injected PTH sample are resolved separately from PTH which migrates as a single large absorbance peak. This enables the essentially pure PTH to be collected as a distinct fraction of eluant, to the exclusion of other material which separates therefrom during column migration. The essentially pure PTH eluted from the reversed phase HPLC column may be lyophilized in the conventional manner, preferably immediately after collection to avoid oxidative inactivation of the PTH.

Once obtained, the CE-grade human PTH may be formulated for therapeutic use. Thus, pharmaceutical compositions containing such PTH may be generated by mixing a desired amount e.g. a unit dose, of the PTH with a sterile and pyrogen-free aqueous vehicle. The aqueous PTH composition may be supplemented with reducing agent such as cysteine, if desired, to resist oxidation and enhance shelf life. Also, since PTH is more stable in an acidic environment, the aqueous vehicle may be acidified using for example acetic acid. The pharmaceutical composition may also be supplemented with an amount of a second therapeutic agent, if desired. For example, an effective amount of either a calcium salt or a vitamin D analogue may be incorporated for use as a bone therapeutic, in the manner described in U.S. Pat. No. 4,698,328.

It will be appreciated that use of PTH in essentially pure form and in a pharmaceutical context offers the distinct advantages of reducing side effects and immunogenicity that may be elicited by contaminants residing in compositions having otherwise lower levels of purity, and of reducing the amount of PTH required to elicit a given physiological response.

It will also be understood that the technique herein described for purifying PTH can be applied to PTH compositions obtained by various techniques, including extraction from mammalian tissue, from microbial sources of PTH and from synthetic sources. Generally, PTH isolated from such sources is obtained in partially purified form i.e. subjected to at least one column fractionation step, before being subjected to the reversed phase HPLC process of the present invention. When obtained from a microbial source such as bacteria for example, the microbial extracts are desirably first treated to concentrate the PTH such as by acid extraction or ammonium sulphate precipitation, and the treated samples are then subjected to any of the various fractionation techniques useful for PTH enrichment. For example, the crude PTH sample may be subjected to ion exchange chromatography e.g. using an S-Sepharose or Mono-S column, or hydrophobic interaction chromatography e.g. using a phenyl-Sepharose column. The extent to which the crude sample is enriched for PTH prior to reversed phase HPLC-based purification will depend to a large extent on the environment in which PTH is produced. In this regard, and in accordance with a preferred embodiment of the invention, the PTH source is desirably an E. coli transformant that has been engineered genetically to produce PTH as a secreted (periplasmic) or as an excreted (extracelluar) product. In a particularly preferred embodiment of the invention, the PTH source is an E. coli transformant which produces PTH as an extracellular product, as described for example by Wong et al in EP 357,391 which is incorporated herein by reference and summarized briefly, infra.

EXAMPLES

In the following examples, analysis and purification were performed, for comparison, on PTH samples obtained from the following various sources:

1) E. coli-excreted PTH: This PTH material was obtained using the PTH production system described by Wong and Sutherland in European patent application 357,391 published 7 Mar. 1990, which is incorporated herein by reference. Briefly, this production system exploits as production host an E. coli JM101 strain that uses the tac promoter to drive expression of a PTH precursor bearing the ompA signal peptide, and that excretes mature human PTH to the medium in which the strain is cultured. Prior to RP-HPLC fractionation, a substantially pure preparation of this "excreted" PTH was obtained in the following manner: whole broth was pH adjusted to 4.0 from 8.0 with glacial acetic acid then clarified by centrifugation. Sample was then loaded onto a 1 liter S-Sepharose column and washed with 4 column volumes of 40 mM ammonium acetate buffer then 6 column volumes of 400 nM ammonium acetate buffer. Column was eluted with gradient of 0.4M-1.0M ammonium acetate buffer over 8 column volumes, and fractions containing PTH (determined by PAGE analysis) were pooled.

Pooled S-Sepharose fractions were then adjusted to pH8.0 with 5N sodium hydroxide and loaded onto a 70 ml phenyl-Sepharose column. The column was washed with 7 column volumes of 0.06M ammonium acetate buffer. Column was eluted with a gradient of 0.6–0.4M ammonium acetate over 10 column volumes. Fractions were collected and pooled based on aliquot testing on C-18 reversed phase HPLC (acetonitrile/TFA) and polyacrylamide gel electrophoresis.

The pooled Phenyl-Sepharose fractions were then analyzed by RP-HPLC in C-18 silica using HFBA as ion-pairing agent, and revealed single peak protein migration suggesting that mature human PTH had been purified (FIG. 2A).

2) E. coli-produced intracellular PTH—This PTH material was produced as described by Sung et al in J. Biol. Chem., 1991, 266(5):2831. Briefly, as reported by these authors, this production systems exploits as host an E. coli Y1090 strain that uses the lac promoter to produce an N-methionyl PTH which is converted endogenously by aminopeptidase to mature human PTH. To extract PTH, cells were disrupted by sonication, and crude PTH was recovered by acid extraction following removal of cellular debris via centrifugation. Extracted PTH was adjusted to about pH 4 using sodium hydroxide, fractionated on a cation exchanger Mono-S column, and pooled samples were then fractionated by reversed phase HPLC in the presence of TFA. Single peak purity of the mature PTH was determined analytically by RP-HPLC in the presence of TFA and in HFBA.

Synthetic PTH—Samples of human PTH produced by solid phase peptide synthesis were purchased from Bachem Inc. (1987–1988 catalogue #PCAL175). According to sample specifications provided by the supplier, the PTH was determined to be greater than 99% pure when analyzed by RP-HPLC using 0.1%TFA as ion-pairing agent.

EXAMPLE 1

Analysis of PTH purity by capillary electrophoresis

With reversed phase HPLC analysis suggesting that the samples obtained as described above represented pure human PTH, the samples were then analyzed using the more sensitive analytical technique of capillary electrophoresis. For this purpose, the capillary electrophoresis device available from Applied Biosystems, Model #270 was used. Samples of PTH recovered from HFBA-based HPLC purification and containing PTH in concentrations ranging from 0.2 mg/ml to 1.0 mg/ml were placed in sample tubes and drawn into the capillary column that had been pre-conditioned with 100 mM phosphate buffer. Conditions employed to effect separation within the capillary were a voltage of +20 Kv. Sample was loaded, by vacuum draw, for from 2-10 seconds.

As is illustrated in FIG. 1, PTH samples appearing pure when analyzed by TFA-and HFBA-based reversed phase HPLC actually contain various species of contaminants that are detectable when analyzed by capillary electrophoresis (CE). FIG. 1A for example shows the CE profile (absorbance at 214nm) of the E. coli-excreted PTH sample that migrates as a single HPLC peak in HFBA. Revealed in the CE profile are four previously undetected minor peaks eluting ahead of the main human PTH peak, and some trailing peaks. Purity of the sample estimated by CE analysis is about 90% (marker peak included). Similarly, in the E. coli-produced intracellular PTH (FIG. 1B) which migrates as a single peak by RP-HPLC/TFA, the CE profile reveals three minor peaks eluting ahead of the PTH main peak, and small trailing peaks for an overall calculated purity of 97.8%. Also, the synthetic PTH (FIG.

1C) generates a CE migration pattern that reveals a large and therefore heterogeneous main peak, with small peaks visible in the leading edge, and an overall purity not exceeding 89%. Represented in the large peak are probably multiple PTH species bearing non-deprotected amino acid residues.

EXAMPLE 2

Purification of human PTH by RP-HPLC using amine-based ion-pairing agent

A sample of the *E. coli*-excreted human PTH (Wong et al, supra) was obtained after fractionation on phenyl-Sepharose as described above in the examples preamble. The sample recovered from the Phenyl-Sepharose column was adjusted from pH8 to pH4 by addition of phosphoric acid, and 200 ul of the pH adjusted sample was injected into the HPLC device (Waters HPLC system as follows: 721 Data Module, 730 Gradient Programmer, two 510 HPLC pumps, U6K manual injector, 440 variable wavelength detector). Incorporated in the device was a column packed with 5u C-18 silica beads sold under the trade name Dynamax by Rainin (4.1×25 cm, 300A pore size). Solvents A and B consisted of 100% water (A) and 80% acetonitrile (B), each supplemented with 0.4% triethylamine and 0.4% phosphoric acid. The automated flow rate was 1 ml/min and the solvents were blended as follows over the indicated time course (minutes):

| time | % A | % B |
|------|-----|-----|
| 0    | 70  | 30  |
| 5    | 70  | 30  |
| 40   | 40  | 60  |
| 45   | 40  | 60  |
| 50   | 70  | 30  |
| 55   | 70  | 30  |

Figure 2B:
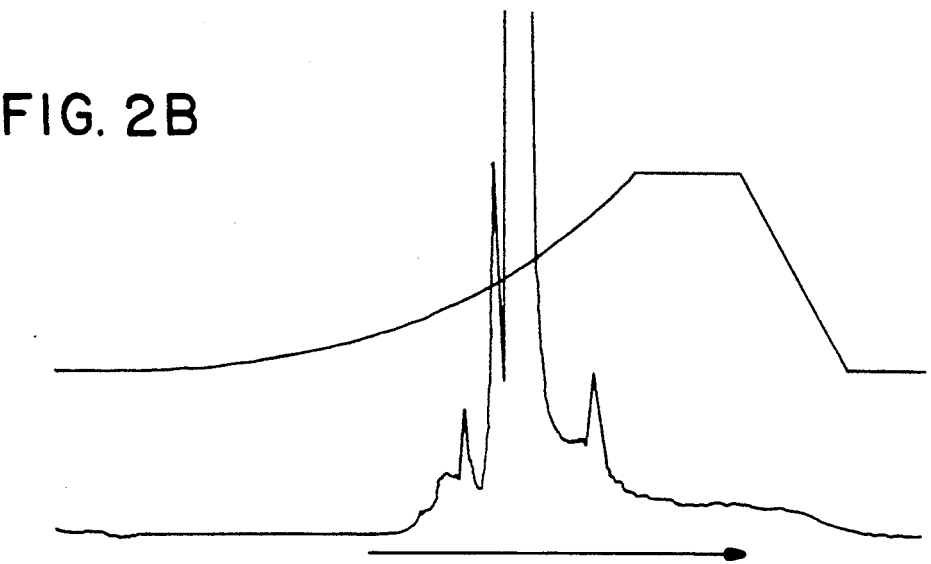
Figure 2C:
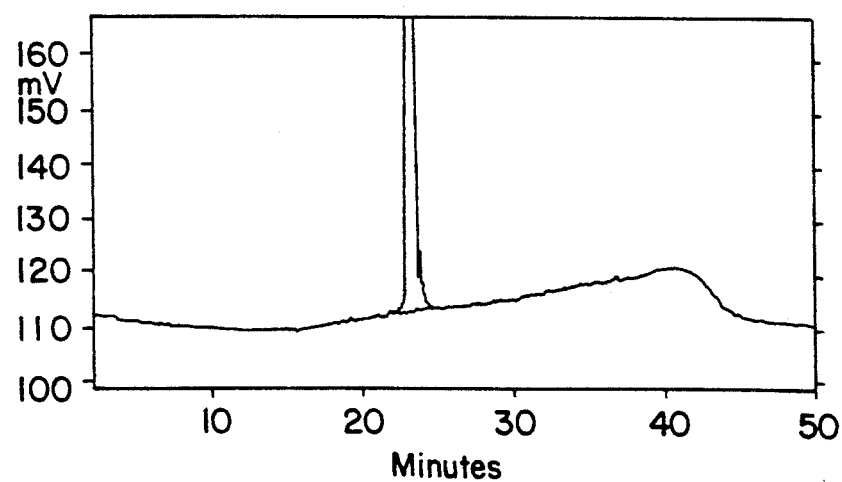
Figure 3A:
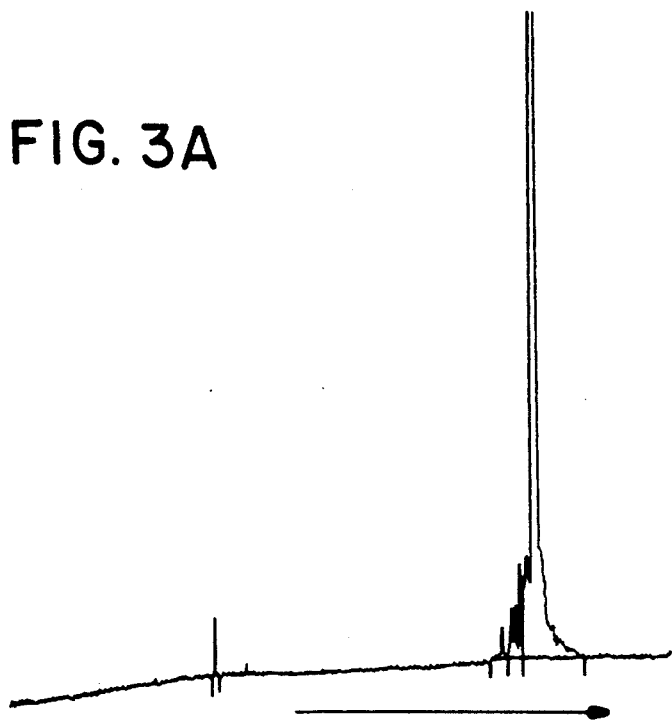
Figure 3B:
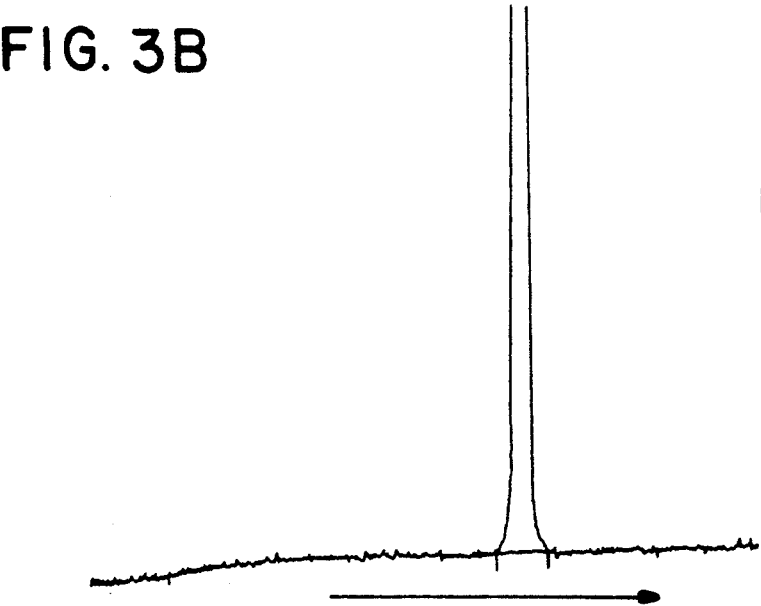

The main PTH peak eluted at 26.62 minutes and 35% acetonitrile, and was well separated from contaminants not previously revealed when HFBA was used as the ion pairing agent. This main absorbance peak was collected for subsequent analysis by capillary electrophoresis, and was also re-run through TEAP-based RP-HPLC in the manner just described. Results of these HPLC analyses are illustrated in FIG. 2, which shows graphically the resolving power of TEAP (FIG. 2B) relative to HFBA (FIG. 2A), and the ability to obtain HPLC grade (single peak) human PTH (FIG. 2C), which is also characterized as single peak by CE (FIG. 3).

The *E. coli*-produced intracellular PTH was also subjected to TEAP-based HPLC purification under these conditions. The chromatogram (not shown) identified two leading peaks of contaminant not separated by fractionation in TFA.

EXAMPLE 3

Analysis of human PTH purity before and after RP-HPLC using amine-based ion-pairing agent For comparison with the HFBA-purified PTH, the TEAP-purified PTH obtained as described in example 2 was analyzed by capillary electrophoresis under the conditions specified in example 1. The comparative results are presented in FIG. 3, which shows multiple absorbance peaks (214 nm) for the HFBA-purified material (FIG. 2A) and a single absorbance peak (214 nm) for the TEAP-purified equivalent (FIG. 2B).

We claim:

1. Essentially pure human parathyroid hormone, characterized by single peak migration when analyzed by capillary electrophoresis at 214 nm, and by an EC50 as determined in the UMR 106-based adenylate cyclase assay of not more than 2 nM.

2. Essentially pure human parathyroid hormone as defined in claim 1, in lyophilized form.

3. A method for preparing a pharmaceutical composition, which comprises the step of combining essentially pure human parathyroid hormone as defined in claim 1, with a pharmaceutically acceptable carrier.

4. A pharmaceutical composition comprising a therapeutically effective amount of essentially pure human parathyroid hormone as defined in claim 1, and a pharmaceutically acceptable carrier.

5. A pharmaceutical composition according to claim 4, wherein said carrier is an aqueous vehicle.

6. A pharmaceutical composition according to claim 5, further comprising a stability-enhancing amount of a reducing agent.

7. A pharmaceutical composition according to claim 4, further comprising a second therapeutic agent.

8. A method for purifying human parathyroid hormone, which comprises the step of fractionating a partially purified human PTH preparation by reversed phase high performance liquid chromatography with a cationic ion-pairing agent.

9. A method according to claim 8, wherein the cationic ion-pairing agent is an amine-based ion pairing agent.

10. The method according to claim 9, wherein the amine-based ion-pairing agent is triethylamine, or a salt thereof.

11. The method according to claim 10, wherein the amine-based ion-pairing agent is triethylamine phosphate.

12. The method according to claim 10 wherein the partially purified parathyroid preparation is obtained from a microbial source of human parathryoid hormone.

13. The method according to claim 12, wherein the microbial source of human parathyroid hormone is a bacterial source of human parathyroid hormone.

14. The method according to claim 13 wherein the bacterial source of human parathyroid hormone is an $E.$ $coli$ source of human parathyroid hormone.

15. Essentially pure human parathyroid hormone obtained by the steps of
  i) obtaining a partially purified preparation of $E.$ $coli$-produced human parathyroid hormone,
  ii) fractionating the partially purified preparation by reversed phase high performance liquid chromatography with triethylamine or a salt thereof; and
  iii) collecting, following the chromatographic step, essentially pure human parathyroid hormone.

16. The method according to claim 13, further comprising the subsequent step of lyophilizing the human parathyroid hormone collected.

17. Essentially pure human parathyroid hormone, obtained by the method according to claim 8.

18. An essentially pure human parathyroid hormone according to claim 1, wherein said EC50 is between about 0.8 nM and about 1.2 nM.

19. Essentially pure human parathyroid hormone as defined in claim 18, in lyophilized form.

20. A method for preparing a pharmaceutical composition, which comprises the step of combining essentially pure human parathyroid hormone as defined in claim 18, with a pharmaceutically acceptable carrier.

21. A pharmaceutical composition comprising a therapeutically effective amount of essentially pure human parathyroid hormone as defined in claim 18, and a pharmaceutically acceptable carrier.

* * * * *